United States Patent
Funakubo

(10) Patent No.: US 9,872,668 B2
(45) Date of Patent: Jan. 23, 2018

(54) MEDICAL DIAGNOSTIC APPARATUS, METHOD FOR OPERATING MEDICAL DIAGNOSTIC APPARATUS, AND COMPUTER-READABLE RECORDING MEDIUM

(71) Applicant: OLYMPUS CORPORATION, Tokyo (JP)

(72) Inventor: Sho Funakubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/632,455

(22) Filed: Jun. 26, 2017

(65) Prior Publication Data

US 2017/0290571 A1    Oct. 12, 2017

Related U.S. Application Data

(63) Continuation of application No. PCT/JP2015/083996, filed on Dec. 3, 2015.

(30) Foreign Application Priority Data

Dec. 26, 2014    (JP) .................. 2014-266388

(51) Int. Cl.
*A61B 8/00* (2006.01)
*A61B 8/08* (2006.01)
(Continued)

(52) U.S. Cl.
CPC .......... *A61B 8/5223* (2013.01); *A61B 8/4444* (2013.01); *A61B 8/5207* (2013.01); *G01S 7/52071* (2013.01); *G06T 7/0012* (2013.01)

(58) Field of Classification Search
CPC ................................ A61B 8/52; A61B 8/5207
See application file for complete search history.

(56) References Cited

U.S. PATENT DOCUMENTS

| 2004/0133107 A1 | 7/2004 | Hashimoto |
| 2014/0206999 A1 | 7/2014 | Ohta et al. |
| 2016/0324504 A1 | 11/2016 | Ohta et al. |

FOREIGN PATENT DOCUMENTS

| JP | 2002-065667 A | 3/2002 |
| JP | 2004-148015 A | 5/2004 |

(Continued)

OTHER PUBLICATIONS

International Search Report dated Feb. 2, 2016 issued in PCT/JP2015/083996.

*Primary Examiner* — Rajeev Siripurapu
(74) *Attorney, Agent, or Firm* — Scully, Scott, Murphy & Presser, P.C.

(57) ABSTRACT

A medical diagnostic apparatus acquires a signal to generate images of an observation target, sequentially generates observation images based on the acquired signal, and causes a display to continuously display the observation images. The apparatus includes: a first storage for storing the observation images in chronological order; input units for receiving a command signal for freezing the observation images on the display; and a second storage for storing correction information for each input unit so as to associate the correction information with each input unit. The apparatus is configured to: identify an input unit that has received the command signal among the input units; determine a correction amount based on a result of identification by the identification unit and the correction information; and select an observation image generated before or after receiving the command signal according to the correction amount, from among the observation images, based on the correction amount.

11 Claims, 9 Drawing Sheets

(51) Int. Cl.
    *G06T 7/00* (2017.01)
    *G01S 7/52* (2006.01)

(56) References Cited

FOREIGN PATENT DOCUMENTS

| | | | |
|---|---|---|---|
| JP | 2007-282957 | A | 11/2007 |
| JP | 2010-042282 | A | 2/2010 |
| JP | 2014-140410 | A | 8/2014 |

| SWITCH ID | CORRECTION AMOUNT $\Delta T$ (SETTING TIME) | |
|---|---|---|
| | MODEL DELAY TIME | CORRECTION TIME |
| 1 | $T_{11}$ | $T_{21}$ |
| 2 | $T_{12}$ | $T_{22}$ |
| 3 | $T_{13}$ | $T_{23}$ |

| SWITCH ID | CORRECTION AMOUNT $\Delta T$ | | |
|---|---|---|---|
| | SETTING TIME | | UNIFORM ADJUSTMENT TIME |
| | MODEL DELAY TIME | CORRECTION TIME | |
| 1 | $T_{11}$ | $T_{21}$ | $T_{31}$ |
| 2 | $T_{12}$ | $T_{22}$ | $T_{31}$ |
| 3 | $T_{13}$ | $T_{23}$ | $T_{31}$ |

FIG.10

| NORMAL OBSERVATION MODE | CORRECTION AMOUNT ΔT (SETTING TIME) | |
|---|---|---|
| SWITCH ID | MODEL DELAY TIME | CORRECTION TIME |
| 1 | $T_{14}$ | $T_{24}$ |
| 2 | $T_{15}$ | $T_{25}$ |
| 3 | $T_{16}$ | $T_{26}$ |

FIG.11

| ULTRASOUND OBSERVATION MODE | CORRECTION AMOUNT ΔT (SETTING TIME) | |
|---|---|---|
| SWITCH ID | MODEL DELAY TIME | CORRECTION TIME |
| 1 | $T_{11}$ | $T_{21}$ |
| 2 | $T_{12}$ | $T_{22}$ |
| 3 | $T_{13}$ | $T_{23}$ |

MEDICAL DIAGNOSTIC APPARATUS, METHOD FOR OPERATING MEDICAL DIAGNOSTIC APPARATUS, AND COMPUTER-READABLE RECORDING MEDIUM

CROSS REFERENCES TO RELATED APPLICATIONS

This application is a continuation of PCT international application Ser. No. PCT/JP2015/083996, filed on Dec. 3, 2015 which designates the United States, incorporated herein by reference, and which claims the benefit of priority from Japanese Patent Application No. 2014-266388, filed on Dec. 26, 2014, incorporated herein by reference.

BACKGROUND

1. Technical Field

The disclosure relates to a medical diagnostic apparatus for observing an observation target using an ultrasound wave, for example. The disclosure also relates to an ultrasound observation system, a method for operating the medical diagnostic apparatus, and a computer-readable recording medium.

2. Related Art

Ultrasound waves have been used to observe characteristics of material or body tissues as observation targets. To be specific, the ultrasound wave is transmitted to an observation target, and an ultrasound echo reflected from the observation target is subjected to predetermined signal processing, thereby acquiring information on characteristics of the observation target.

In order to diagnose a body tissue using the ultrasound waves, an ultrasound endoscope having an ultrasound transducer at a distal end of an insertion portion is used. A practitioner, such as a doctor, operates an operating unit near the hand after inserting the insertion portion into a body to obtain an ultrasound echo using the ultrasound transducer, and performs diagnosis using information obtained based on the ultrasound echo (ultrasound image).

At the time of diagnosis, a plurality of acquired ultrasound images is displayed on a monitor in chronological order. The practitioner operates a freeze instruction unit and selects an ultrasound image as a freeze display target in order to display a desired image such as an image to be used for diagnosis. As such a diagnostic device, disclosed is a technique in which a desired image is extracted in response to an operation timing of a freeze instruction unit and the extracted image is displayed as a freeze image (for example, see JP 2002-65667 A). According to JP 2002-65667 A, it is possible to display the image that a practitioner desires on a monitor as the freeze image by extracting an image traced back by a delay time, caused until the image is selected from a storage unit through internal processing of the diagnostic device after the freeze instruction unit is operated, from the storage unit.

SUMMARY

In some embodiments, provided is a medical diagnostic apparatus for acquiring a signal to generate images of an observation target, sequentially generating a plurality of observation images based on the acquired signal, and causing an external display unit to continuously display the plurality of observation images. The medical diagnostic apparatus includes: a first storage unit configured to store the plurality of observation images in chronological order; a plurality of freeze instruction input units configured to receive a command signal for freezing the plurality of observation images on the display unit; a second storage unit configured to store correction information for each of the plurality of freeze instruction input units so as to associate the correction information with each of the plurality of freeze instruction input units in advance; an identification unit configured to identify a freeze instruction input unit that has received the command signal among the plurality of freeze instruction input units; a correction amount determining unit configured to determine a correction amount based on a result of identification by the identification unit and the correction information stored in the second storage unit; and an image selection unit configured to select an observation image generated before receiving the command signal according to the correction amount or an observation image generated after receiving the command signal according to the correction amount, from among the plurality of observation images stored in the first storage unit, based on the correction amount determined by the correction amount determining unit.

In some embodiments, provided is a method for operating a medical diagnostic apparatus for acquiring a signal to generate images of an observation target, sequentially generating a plurality of observation images based on the acquired signal, and causing an external display unit to continuously display the plurality of observation images. The method includes: receiving, by a first freeze instruction input unit or a second freeze instruction input unit different from the first freeze instruction input unit, a command signal for freezing the plurality of observation images on the display unit; identifying, by an identification unit, which of the first and second freeze instruction input units have received the command signal; determining, by a correction amount determining unit, a correction amount based on a result of identification; and selecting, by an image selection unit, an observation image generated before receiving the command signal according to the correction amount or an observation image generated after receiving the command signal according to the correction amount, from among the plurality of observation images in accordance with the result of identification.

In some embodiments, provided is a non-transitory computer-readable recording medium with an executable program stored thereon for operating a medical diagnostic apparatus for acquiring a signal to generate images of an observation target, sequentially generating a plurality of observation images based on the acquired signal, and causing an external display unit to continuously display the plurality of observation images. The program causes the medical diagnostic apparatus to execute: receiving, by a first freeze instruction input unit or a second freeze instruction input unit different from the first freeze instruction input unit, a command signal for freezing the plurality of observation images on the display unit; identifying, by an identification unit, which of the first and second freeze instruction input units have received the command signal; determining, by a correction amount determining unit, a correction amount based on a result of identification; and selecting, by an image selection unit, an observation image generated before receiving the command signal according to the correction amount or an observation image generated after receiving the command signal according to the correction amount, from among the plurality of observation images in accordance with the result of identification.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 10 is a table for describing a correction amount stored in a correction amount storage unit of the ultrasound endoscopic system according to the third embodiment of the present invention;

FIG. 11 is a table for describing a correction amount stored in the correction amount storage unit of the ultrasound endoscopic system according to the third embodiment of the present invention.

DETAILED DESCRIPTION

Exemplary embodiments of the present invention will be described below with reference to the appended drawings. Reference will be made to an exemplary ultrasound diagnostic system or an exemplary ultrasound endoscopic system including a medical diagnostic apparatus for generating an ultrasound image based on an ultrasound echo, but the present invention is not limited to the embodiments. The same reference signs are used to designate the same elements throughout the drawings.

First Embodiment

Figure 1:
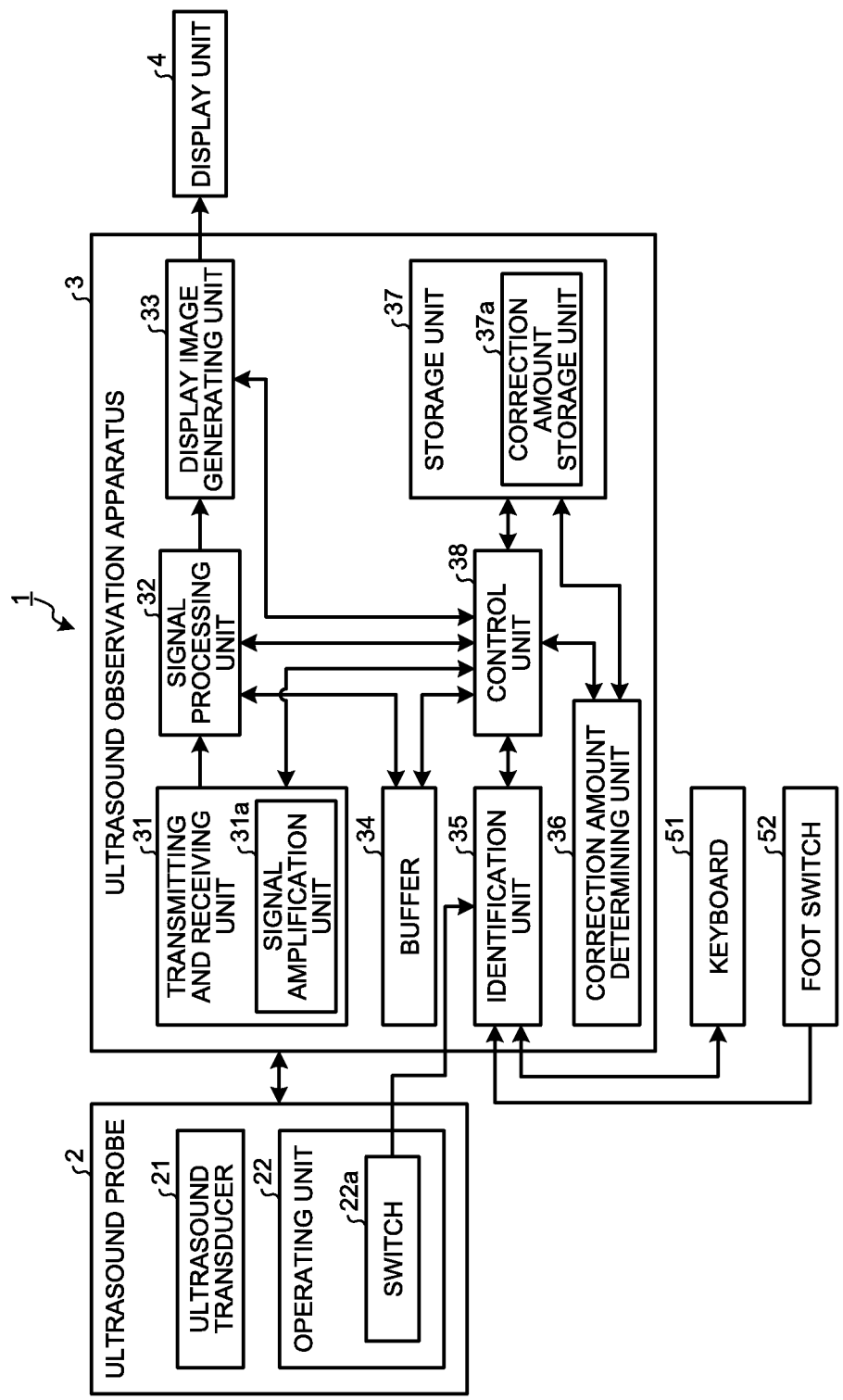
FIG. 1 is a block diagram illustrating a configuration of an ultrasound diagnostic system according to a first embodiment of the present invention.

FIG. 1 is a block diagram illustrating a configuration of an ultrasound diagnostic system according to a first embodiment of the present invention. An ultrasound diagnostic system 1 in FIG. 1 is a device configured to observe an observation target using an ultrasound wave, and corresponds to a medical diagnostic apparatus according to the present invention.

The ultrasound diagnostic system 1 includes an ultrasound probe 2 that outputs ultrasound waves and receives reflected ultrasound echoes, an ultrasound observation apparatus 3 that generates each image based on the ultrasound echoes acquired by the ultrasound probe 2, a display unit 4 that displays various types of information including the images based on the ultrasound echoes generated by the ultrasound observation apparatus 3, and a keyboard 51 and a foot switch 52 which are configured to perform input of various instructions including a freeze command signal. The display unit 4 is implemented using a display panel made of liquid crystal or organic electro luminescence (EL).

The ultrasound probe 2 is configured of a distal end portion which includes an ultrasound transducer 21, which outputs an ultrasound pulse to an observation target and receives an ultrasound echo reflected from the observation target, at a distal end, and an operating unit 22 to operate the ultrasound transducer 21.

Here, when the observation target is a body tissue, the ultrasound transducer 21 may be used in any form of an external probe for emitting an ultrasound wave from a surface of a living body, a miniature ultrasound probe including an elongated insertion portion to be inserted into lumen such as a digestive tract, a biliopancreatic duct, or a blood vessel, and an ultrasound endoscope further including an optical system in an intraluminal ultrasound probe. When the ultrasound endoscope is employed among these, the ultrasound transducer 21 is provided on a distal end side of the insertion portion of the intraluminal ultrasound probe, and the intraluminal ultrasound probe is connected to a processing device on a proximal end side in a detachable manner.

The ultrasound transducer 21 converts an electrical pulse signal received from the ultrasound observation apparatus 3 into an ultrasound pulse (acoustic pulse signal), and further, converts the ultrasound echo reflected from an external specimen into an electrical echo signal. The ultrasound transducer 21 may be configured to cause an ultrasound transducer to mechanically perform scanning or to cause a plurality of ultrasound transducers to electronically perform scanning.

The operating unit 22 includes a bending knob to bend the distal end of the ultrasound probe 2, a treatment instrument insertion portion through which a treatment instrument such as biological forceps, an electric scalpel, and an inspection probe is inserted into a subject, and a plurality of switches serving as an operational input unit to input an operational command signal with respect to the ultrasound observation apparatus 3. The plurality of switches include a switch 22a configured to input a freeze instruction of the images based on the ultrasound echoes displayed on the display unit 4.

The ultrasound observation apparatus 3 includes a transmitting and receiving unit 31, a signal processing unit 32 (image selection unit), a display image generating unit 33, a buffer 34 (first storage unit), an identification unit 35, a correction amount determining unit 36 (selection designated time deciding unit), a storage unit 37, and a control unit 38.

The transmitting and receiving unit 31 performs reception and transmission of an electric signal with the ultrasound transducer 21. The transmitting and receiving unit 31 is electrically connected with the ultrasound transducer 21, transmits the electrical pulse signal to the ultrasound transducer 21, and receives the echo signal as an electrical reception signal from the ultrasound transducer 21. To be specific, the transmitting and receiving unit 31 generates the electrical pulse signal based on a waveform and a transmission timing, set in advance, and transmits the generated pulse signal to the ultrasound transducer 21.

The transmitting and receiving unit 31 includes a signal amplification unit 31a that amplifies the echo signal. The signal amplification unit 31a performs sensitivity time control (STC) correction to amplify an echo signal having a larger reception depth with a higher amplification factor. The transmitting and receiving unit 31 performs processing such as filtering to the echo signal amplified by the signal amplification unit 31a, and then, performs A/D conversion to the echo signal to generate and output a digital radio frequency (RF) signal in a time domain.

The signal processing unit 32 performs signal processing with respect to the electrical echo signal. To be specific, the signal processing unit 32 generates B-mode image data as an ultrasound image (observation image) obtained by converting amplitude of the echo signal to a luminance and displaying the converted signal. The signal processing unit 32 generates the B-mode image data by causing a digital signal to be subjected to the signal processing using a known technique such as a band-pass filter, logarithmic conversion, gain processing, and contrast processing. A B-mode image is a grayscale image having equal R (red), G (green), and B (blue) values, which are variables in an RGB color system employed as a color space.

The signal processing unit 32 outputs the B mode image data, generated by sequentially performing the signal processing to the digital RF signals output from the transmitting and receiving unit 31, to the display image generating unit 33 and outputs the generated B mode image data to the buffer 34. In addition, when there is the input of the freeze command signal of the image, the signal processing unit 32 functions as an image selection unit that extracts, from the buffer 34, the B mode image data traced back by a correction amount based on the correction amount (correction time) determined by the correction amount determining unit 36, and outputs an extracted B mode image to the display image generating unit 33 as a freeze image. The signal processing unit 32 may output the B mode image extracted as the freeze image to the storage unit 37 according to a command signal from the control unit 38 or the like to cause the storage unit 37 to store the image. In addition, a processing block (image selection unit) to perform image selection may be additionally provided separately from the signal processing unit 32.

The display image generating unit 33 performs predetermined processing, such as decimation of data in response to a data step width set according to a display range of an image in the display unit 4 and gradation processing, to the B mode image data generated by the signal processing unit 32, and then, outputs the processed signal as display image data for display. The display image generating unit 33 causes the B mode image data sequentially output from the signal processing unit 32 to be subjected to the above-described processing and be displayed on the display unit 4 in real time, and causes the B mode image data output from the signal processing unit 32 as the freeze image to be subjected to the above-described processing and to be displayed as a still image on the display unit 4.

The buffer 34 is implemented using, for example, a ring buffer, and stores a certain amount (a predetermined number of frames) of the B mode image data generated by the signal processing unit 32 in chronological order. When the capacity is insufficient (the predetermined number of frames of the B mode image data are stored), the predetermined number of frames of the latest B mode image data are stored in a time-series order by overwriting the latest B mode image data on the oldest B mode image data.

The identification unit 35 detects a signal input from the keyboard 51 and the foot switch 52. When the detected signal is the freeze command signal of the image, the identification unit 35 identifies a switch ID and outputs information relating to the switch ID to the control unit 38 together with the freeze command signal.

When there is the input of the freeze command signal of the image, the correction amount determining unit 36 determines the correction amount for selection of the B mode image serving as the freeze target image with reference to the storage unit 37. To be specific, the correction amount determining unit 36 determines a correction time (selection designated time) for selection of the B mode image obtained by tracing back from the B mode image at an input timing of the freeze command signal, by a predetermined time (predetermined frame), with reference to the storage unit 37 based on the switch ID identified by the identification unit 35.

The storage unit 37 stores data including various programs to operate the ultrasound diagnostic system 1, various parameters necessary for an operation of the ultrasound diagnostic system 1, and the like. The storage unit 37 includes a correction amount storage unit 37a (second storage unit).

Figures 2, 3:
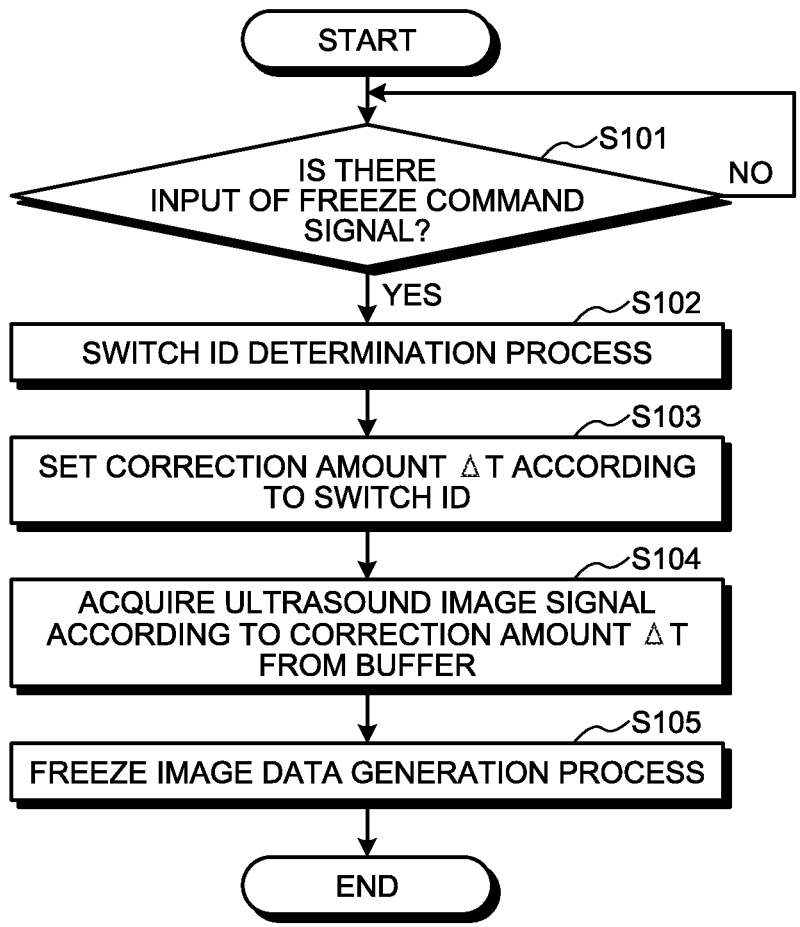
FIG. 2 is a table for describing a correction amount stored in a correction amount storage unit of the ultrasound diagnostic system according to the first embodiment of the present invention.
FIG. 3 is a flowchart for describing a freeze image generation process performed by an ultrasound observation apparatus according to the first embodiment of the present invention.

The correction amount storage unit 37a stores the correction time for selection of the freeze target image in association with the switch ID identified by the identification unit 35. In the first embodiment, a setting time, which is a sum of a model delay time to be described later and the correction time, is the correction amount. FIG. 2 is a table for describing the correction amount stored in the correction amount storage unit of the ultrasound diagnostic system according to the first embodiment. As illustrated in FIG. 2, a correction amount $\Delta T$ is stored for each switch ID. In the first embodiment, a switch ID:1 is associated with the switch 22a of the operating unit 22, a switch ID:2 is associated with the foot switch 52, and a switch ID:3 is associated with a freeze instruction input key of the keyboard 51.

The correction amount $\Delta T$ is calculated as the sum of the model delay time and the correction time. The model delay time (model delay times $T_{11}$ to $T_{13}$) is set according to a processing time required for specific signal processing of a model, and corresponds to, for example, a processing time between press of the foot switch 52 and selection (extraction) of the freeze target image. The correction time (correction times $T_{21}$ to $T_{23}$) is the time that can be arbitrarily set by the practitioner or the like, and the time configured to adjust the model delay time according to the own freeze instruction timing. The correction amount $\Delta T$ is the time temporally in the past or future than a time phase of a timing at which the freeze instruction is input based on the correction time, that is, the time obtained by tracing back from a reception time of the input of the freeze instruction by a predetermined time or elapsed time. In this manner, the correction amount $\Delta T$ has been set for each switch ID (models) in the first embodiment. The above-described setting time also includes a case where the correction times $T_{21}$ to $T_{23}$ are zero. That is, the setting time may be configured only using the model delay times $T_{11}$ to $T_{13}$. In addition, the correction amount $\Delta T$ may be set as a traced time by designating the number of frames to be traced instead of time.

The storage unit 37 stores the various programs including an operation program configured to execute an operation method of the ultrasound diagnostic system 1. The operation program can be recorded in a computer-readable recording medium, such as a hard disk, a flash memory, a CD-ROM, a DVD-ROM, and a flexible disk, to be widely distributed. The above-described various programs can be acquired by download via a communication network. The communication network used here is implemented, for example, using an existing public switched telephone network, local area network (LAN), wide area network (WAN), or the like, which may be wired or wireless.

The storage unit 37 having the above-described configuration is implemented using a read only memory (ROM) in which the various programs and the like are installed in advance, a random access memory (RAM) which stores a calculation parameter and data of each processing, and the like.

The control unit 38 is implemented using a central processing unit (CPU), various calculation circuits, and the like having a control function. The control unit 38 reads information stored and saved in the storage unit 37 from the storage unit 37, and executes various types of calculation processing relating to the operation method of the ultrasound diagnostic system 1 so as to collectively control the ultrasound diagnostic system 1.

The keyboard 51 is provided with a key, and outputs a signal in response to the key when the key is pressed. The keyboard 51 may be configured to implement the key using a touch panel, and to include a display unit to display the image.

The foot switch 52 includes a bar that receives input of a signal when being stepped on by a foot. In the first embodiment, when the practitioner steps on the bar, the freeze command signal of the image is received, and the freeze command signal is input to the identification unit 35. This freeze command signal also includes the information on the switch ID of the foot switch 52. In the first embodiment, the switch 22a, the keyboard 51, and the foot switch 52 correspond to freeze instruction input units. Next, reference will be made to a freeze image generation process that is performed by the ultrasound observation apparatus 3 of the ultrasound diagnostic system 1 having the above-described configuration with reference to the drawings. FIG. 3 is a flowchart for describing the freeze image generation process performed by an ultrasound observation apparatus according to the first embodiment. The following freeze image generation process will be described assuming that the B mode images sequentially generated by the display image generating unit 33 are displayed in real time as the premise.

First, the control unit 38 determines whether there is the input of the freeze command signal (Step S101: a freeze instruction input step). When there is the input of the freeze command signal (Step S101: Yes), the control unit 38 proceeds to Step S102. On the contrary, when there is no input of the freeze command signal (Step S101: No), the control unit 38 returns to Step S101 and repeatedly checks the input of the freeze command signal. The case where there is no input of the freeze command signal includes a case where there is input of a command signal and the command signal is a signal instructing a function other than the freeze instruction. When the command signal instructing a function other than the freeze instruction is input, the control unit 38 performs different processing according to the command signal.

After transitioning to Step S102 the control unit 38 determines the switch ID of the switch that has input the freeze command signal (an identification step). The control unit 38 causes the identification unit 35 to identify the switch ID assigned to the freeze command signal. When obtaining an identification result from the identification unit 35, the control unit 38 outputs the identification result (the switch ID) to the correction amount determining unit 36 and proceeds to Step S103.

In Step S103, the correction amount determining unit 36 determines the correction amount, and performs setting of the determined correction amount (the correction amount $\Delta T$) (a selection designated time decision step). To be specific, the correction amount determining unit 36 refers to the correction amount storage unit 37a based on the switch ID identified by the identification unit 35 to output the correction amount $\Delta T$, and sets the correction amount $\Delta T$ corresponding to the freeze command signal (the switch ID).

When the correction amount $\Delta T$ is set by the correction amount determining unit 36, the control unit 38 outputs the correction amount $\Delta T$ to the signal processing unit 32 to output the B mode image data (ultrasound image signal) corresponding to the correction amount $\Delta T$ (Step S104: an image selection step). To be specific, the signal processing unit 32 extracts (acquires) the B mode image data obtained by tracing back from a B mode image (frame number), displayed on the display unit 4 at an input timing (time) of the freeze command signal, by a predetermined time (or a predetermined frame) from the buffer 34 and outputs the extracted data to the display image generating unit 33.

Figures 4, 5:
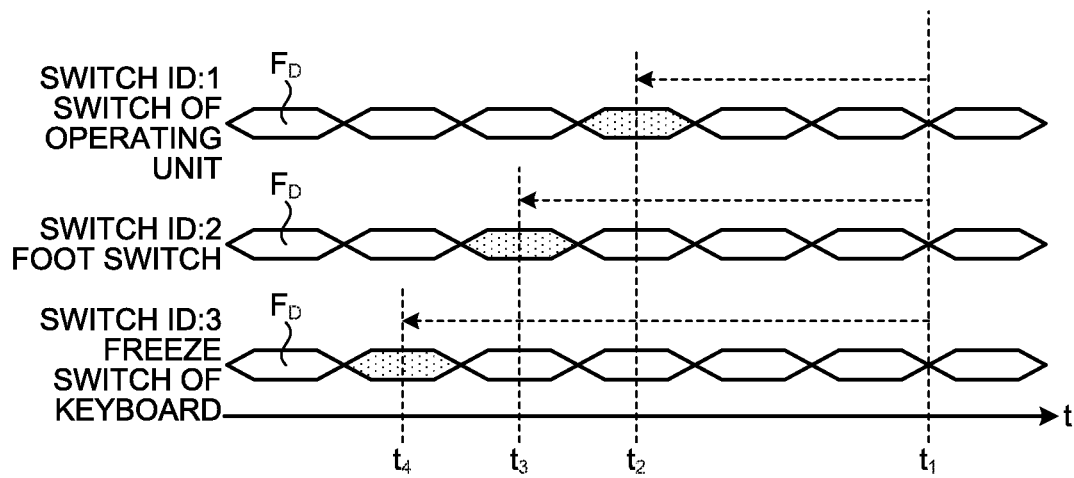
FIG. 4 is a diagram for describing image selection in the freeze image generation process according to the first embodiment of the present invention.
FIG. 5 is a table for describing a setting time and a uniform adjustment time stored in a correction amount storage unit of an ultrasound diagnostic system according to a modified example of the first embodiment of the present invention.

FIG. 4 is a diagram for describing image selection in the freeze image generation process according to the first embodiment, and is a schematic diagram illustrating frame data $F_D$, which corresponds to time-series (time t) B mode image data stored in the buffer 34, for each switch ID. As illustrated in FIG. 4, when the freeze instruction is input by the practitioner at time $t_1$, for example, the signal processing unit 32 extracts the frame data $F_D$ based on the correction amount $\Delta T$ set by the correction amount determining unit 36. In the case of the switch ID:1 (the switch 22a), for example, the frame data $F_D$, which corresponds to a time $t_2$ obtained by tracing back from the time $t_1$ by $\Delta T$ ($T_{11}+T_{21}$) associated with the switch ID:1 is extracted. In addition, the frame data $F_D$, which corresponds to a time $t_3$ obtained by tracing back by $\Delta T$ ($T_{12}+T_{22}$) associated with the switch ID:2 is extracted in the case of the switch ID:2 (the foot switch 52). In addition, the frame data $F_D$, which corresponds to a time $t_4$ obtained by tracing back by $\Delta T$ ($T_{13}+T_{23}$) associated with the switch ID:3 is extracted in the case of the switch ID:3 (the freeze instruction input key (freeze switch) of the keyboard 51).

Thereafter, the display image generating unit 33 performs predetermined signal processing on the B mode image data output, as the freeze image, from the signal processing unit 32, and performs a process of generating freeze image data for display (Step S105).

The B mode image as the freeze image, generated by performing the freeze image generation process using the ultrasound observation apparatus 3 as described above, enables acquisition of the B mode image data traced back by each correction amount (correction time) with respect to the freeze instruction input by any of the plurality of switches (switches ID:1 to 3), and thus, it is possible to display the freeze image that the practitioner desires on the display unit 4.

According to the first embodiment described above, the correction amount ΔT is set for each of the plurality of switches, and the B mode image data traced in response to the identified switch ID is selected as the freeze image, and thus, it is possible to select a desired image even in the case of using the plurality of freeze instruction units.

The identification unit 35 identifies the switch ID in the first embodiment, but may identify an observation mode (for example, a mode of observing a structure or a mode of observing the blood flow) in addition to the switch ID. In addition, the correction amount determining unit 36 determines the correction amount ΔT based on the observation mode and the identified switch ID if the observation mode is set in advance. In such cases, the correction amount storage unit 37a stores the correction amount ΔT for each of the observation modes.

Modified Example of First Embodiment

Next, a modified example of the first embodiment of the present invention will be described with reference to the drawings. FIG. 5 is a table for describing a setting time and a uniform adjustment time stored in a correction amount storage unit of an ultrasound diagnostic system according to a modified example of the first embodiment. In the above-described first embodiment, the correction amount ΔT according to each switch ID is set by individually setting the correction times $T_{21}$ to $T_{23}$. In the modified example, the respective correction amounts ΔT according to the respective switches ID are collectively changed.

As illustrated in FIG. 5, the correction amount ΔT according to the modified example is calculated as a sum of the model delay time and the correction time (setting time), described above, and a uniform adjustment time. A uniform adjustment time $T_{31}$ can be arbitrarily set by the practitioner. It is possible to collectively cause the correction amounts ΔT of the respective switches ID to be increased from the setting time by the same amount of time by setting the uniform adjustment time $T_{31}$.

Figure 6:
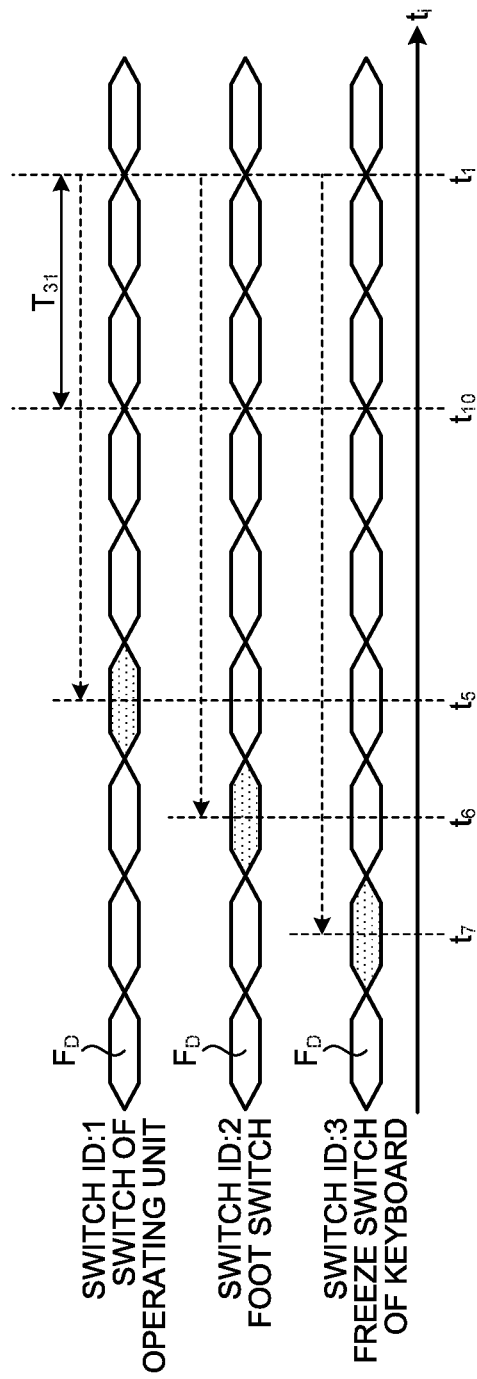
FIG. 6 is a diagram for describing image selection in a freeze image generation process according to the modified example of the first embodiment of the present invention.

FIG. 6 is a diagram for describing image selection in a freeze image generation process according to the modified example of the first embodiment, and is a schematic diagram illustrating frame data $F_D$, which corresponds to time-series (time t) B mode image data stored in the buffer 34, for each switch ID. As illustrated in FIG. 6, when the freeze instruction is input by the practitioner at time $t_1$, for example, the signal processing unit 32 extracts the frame data $F_D$ based on the correction amount ΔT set by the correction amount determining unit 36. In the modified example, the uniform time (uniform adjustment time $T_{31}$) is assigned to the setting time (the model delay time+the correction time) set for each switch ID, and each of the setting time is traced back by the uniform adjustment time $T_{31}$ (time $t_{10}$). In the case of the switch ID:1 (the switch 22a), for example, the frame data $F_D$, which corresponds to a time $t_5$ obtained by tracing back from the time $t_1$ by ΔT ($T_{11}+T_{21}+T_{31}$) associated with the switch ID:1 is extracted. In addition, the frame data $F_D$, which corresponds to a time $t_6$ obtained by tracing back by ΔT ($T_{12}+T_{22}+T_{31}$) associated with the switch ID:2 is extracted in the case of the switch ID:2 (the foot switch 52). In addition, the frame data $F_D$, which corresponds to a time $t_7$ obtained by tracing back by ΔT ($T_{13}+T_{23}+T_{31}$) associated with the switch ID:3 is extracted in the case of the switch ID:3 (the freeze instruction input key of the keyboard 51).

According to the modified example, the respective correction amounts ΔT of the respective switches ID are collectively increased by setting the uniform adjustment time $T_{31}$, and thus, it is possible to change the correction amount ΔT without changing a relative relationship (difference) among the correction times $T_{21}$ to $T_n$ that have been individually set. For example, it is possible to easily perform resetting of the correction amount ΔT in a case where different practitioners change the correction amount ΔT while maintaining a relationship among $T_{11}+T_{21}$, $T_{12}+T_{22}$, and $T_{13}+T_{23}$, or in a case where image quality or a frame rate differs due to a specification difference between devices. When the uniform adjustment time $T_{31}$ is set according to the image quality or the frame rate, it is possible to display the freeze image that the practitioner desires on the display unit 4 in response also to the specification difference between devices and the like.

Second Embodiment

Figure 7:
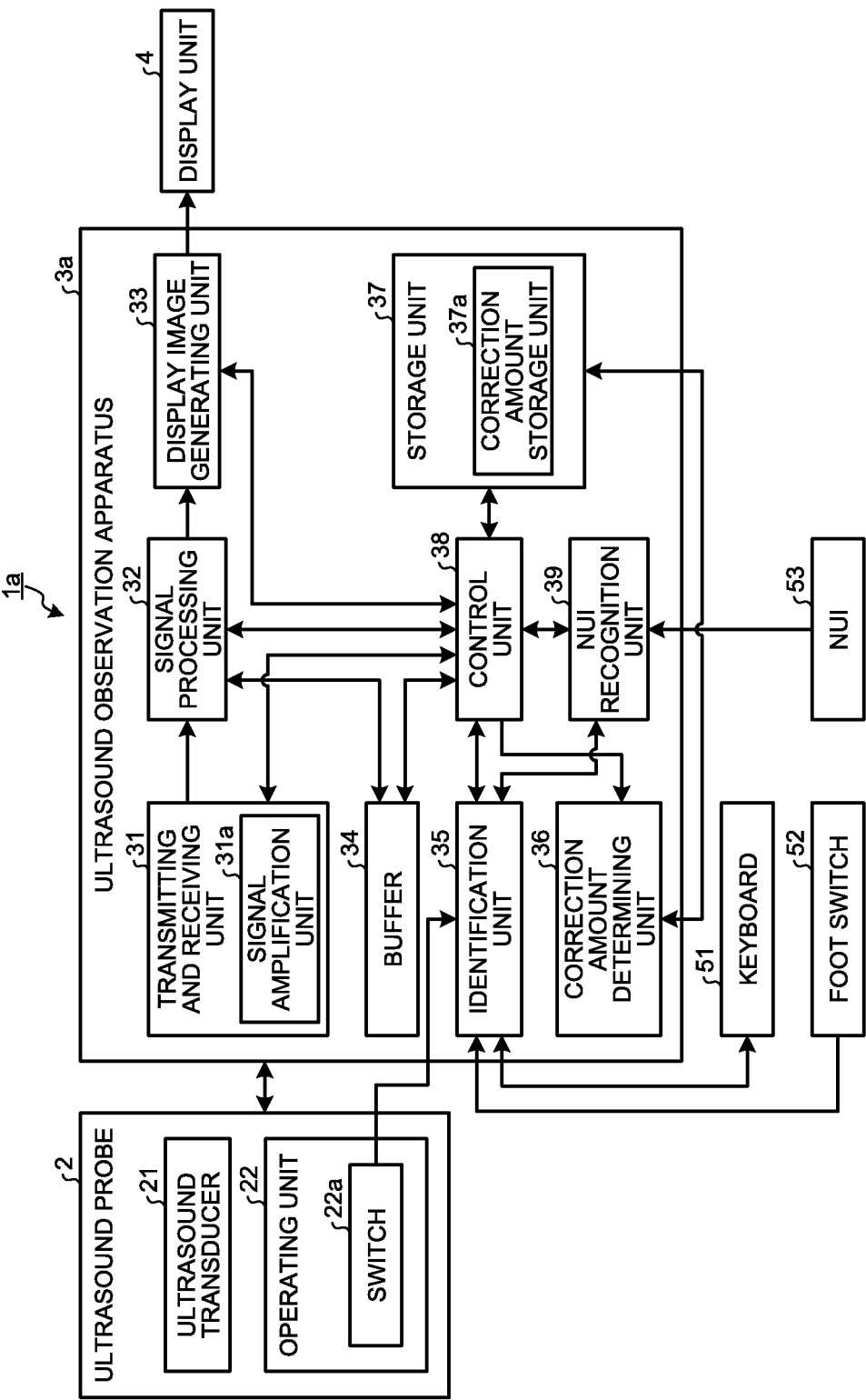
FIG. 7 is a block diagram illustrating a configuration of an ultrasound diagnostic system according to a second embodiment of the present invention.

Next, a second embodiment of the present invention will be described. FIG. 7 is a block diagram illustrating a configuration of an ultrasound diagnostic system according to the second embodiment. The same reference signs are used to designate the same elements as those of the above-described embodiment. In the above-described first embodiment, the freeze instruction is input using the keyboard 51 and the foot switch 52. In the second embodiment, a non-contact user interface to input the freeze instruction using voice is provided in addition to the keyboard 51 and the foot switch 52.

An ultrasound diagnostic system 1a according to the second embodiment includes the above-described ultrasound probe 2, an ultrasound observation apparatus 3a that generates each image based on ultrasound echoes acquired by the ultrasound probe 2, the display unit 4 that displays various types of information including the images based on the ultrasound echoes generated by the ultrasound observation apparatus 3a, and the keyboard 51, the foot switch 52, and a natural user interface (NUI) 53, as the non-contact user interface, which are configured to perform input of various instructions including a freeze command signal. In the second embodiment, the NUI 53 is implemented using, for example, a microphone, and converts voice (sound) generated by a practitioner or the like into an electric signal. The above-described switch ID is also assigned in the NUI 53.

The ultrasound observation apparatus 3a includes a NUI recognition unit 39 that recognizes the electric signal converted by the NUI 53 in addition to the configuration of the ultrasound observation apparatus 3 according to the above-described first embodiment.

The NUI recognition unit 39 detects a frequency of voice input to the NUI 53 (microphone), and compares the detected voice frequency and feature data stored in advance to output a language group as a recognition result. To be specific, when "freeze" is input by the practitioner to the NUI 53, for example, the NUI recognition unit 39 recognizes "freeze" by comparing the obtained electric signal with the feature data, and outputs a command relating to a freeze instruction of an image to the identification unit 35 as a recognition result.

Figure 8:
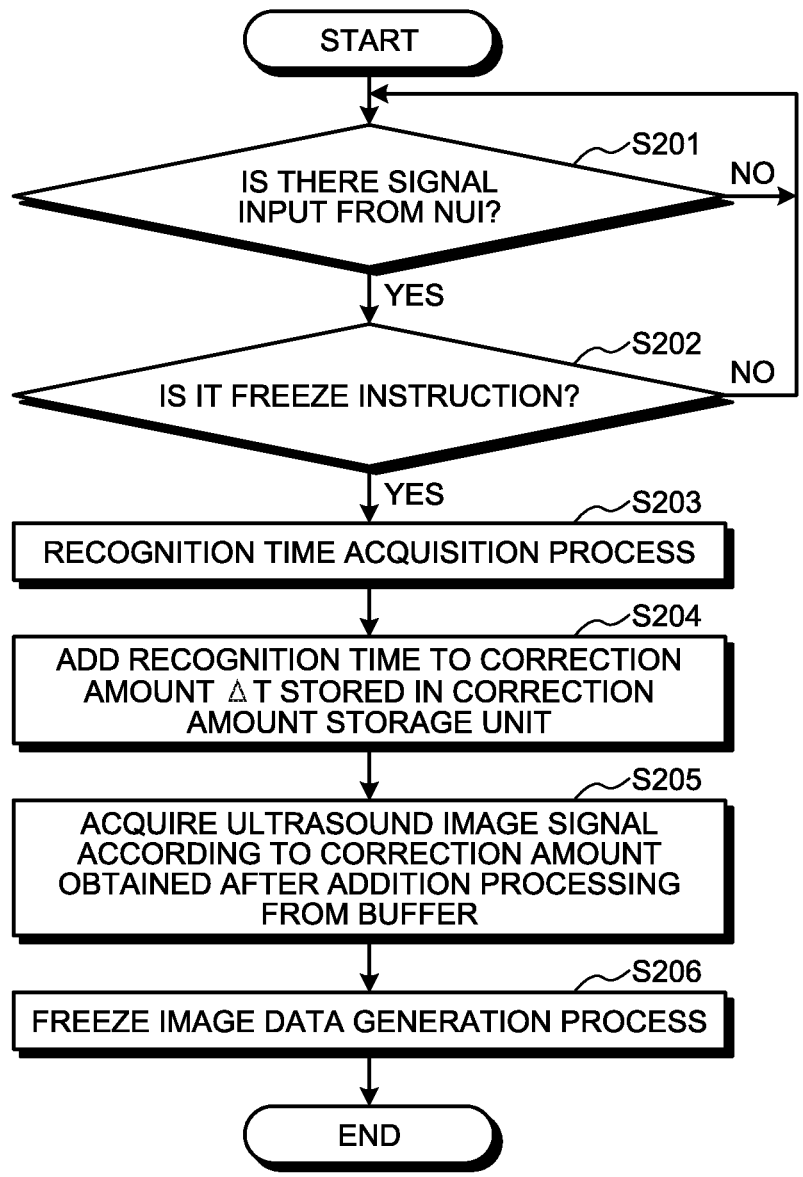
FIG. 8 is a flowchart for describing a freeze image generation process performed by an ultrasound observation apparatus according to the second embodiment of the present invention.

Next, reference will be made to a freeze image generation process that is performed by the ultrasound observation apparatus 3a of the ultrasound diagnostic system 1a having the above-described configuration with reference to the drawings. FIG. 8 is a flowchart for describing the freeze image generation process performed by the ultrasound observation apparatus according to the second embodiment. The flowchart illustrated in FIG. 8 describes a case where there is input of a signal from the NUI 53. The freeze image generation process according to the other input units is performed based on the above-described flowchart (see FIG. 3).

First, the control unit 38 determines whether there is the input of the signal from the NUI 53 (Step S201). When there is the input of the signal from the NUI 53 (Step S201: Yes), the control unit 38 proceeds to Step S202. On the contrary, when there is no input of the signal from the NUI 53 (Step S201: No), the control unit 38 returns to Step S201 and repeatedly checks the signal input from the NUI 53.

In Step S202, the control unit 38 determines whether the signal acquired from the NUI 53 (the recognition result obtained by the NUI recognition unit 39) is the freeze instruction. When the command relating to the freeze instruction of the image is detected from the recognition result included in the signal, the control unit 38 determines that it is the freeze instruction (Step S202: Yes), and proceeds to Step S203. In addition, when the signal acquired from the NUI 53 is not the freeze instruction (Step S202: No), the control unit 38 returns to Step S201 and repeatedly checks the signal input from the NUI 53. In the second embodiment, a process of identifying any used input unit between the NUI 53 or another input unit among the respective input units may be set as an identification step, or the reception of the freeze command signal from the NUI 53 may be set as the identification step.

In Step S203, the control unit 38 acquires a recognition time of the NUI 53. To be specific, the control unit 38 acquires a recognition start time at which the NUI 53 has recognized the voice relating to the freeze instruction. The control unit 38 outputs the acquired recognition start time to the correction amount determining unit 36.

Thereafter, the correction amount determining unit 36 determines a correction amount and performs setting of the determined correction amount (correction amount $\Delta T$). To be specific, the correction amount determining unit 36 outputs the correction amount $\Delta T$ according to the NUI 53 with reference to the correction amount storage unit 37a, and adds a time (hereinafter, referred to as a recognition time $T_{20}$), between the recognition start time and a time (recognition completion time) at which the identification unit 35 outputs the freeze command signal to the control unit 38, to the correction amount $\Delta T$ (Step S204). The correction amount determining unit 36 outputs the correction time, obtained by adding the recognition time $T_{20}$ to the correction amount $\Delta T$ (setting time), to the control unit 38 as the correction amount.

When the correction amount (the correction amount $\Delta T$+the recognition time $T_{20}$) obtained after the addition processing performed by the correction amount determining unit 36 is set, the control unit 38 outputs the correction amount to the signal processing unit 32 and extracts (acquires) and outputs B mode image data (an ultrasound image signal) from the buffer 34 (Step S205). The signal processing unit 32 extracts the frame data $F_D$ based on the correction amount set by the correction amount determining unit 36 in the same manner as in the above-described first embodiment. The signal processing unit 32 adds the recognition time $T_{20}$ to the correction amount $\Delta T$ set in advance, and extracts the frame data $F_D$ which corresponds to the time obtained by tracing back from the input time of the freeze instruction by the correction time that has been added with the recognition time $T_{20}$.

Thereafter, the display image generating unit 33 performs predetermined signal processing on the B mode image data output, as the freeze image, from the signal processing unit 32, and performs a process of generating freeze image data for display (Step S206).

The B mode image as the freeze image, generated by performing the freeze image generation process using the ultrasound observation apparatus 3a as described above, enables acquisition of the B mode image data traced back by the time obtained by adding the recognition time $T_{20}$ to the correction amount $\Delta T$ set in advance in a case where the device that has input the freeze instruction is the NUI 53. Thus, it is possible to display the freeze image that the practitioner desires on the display unit 4 even in the case of using the NUI 53 that requires time until recognizing the freeze instruction as compared to the keyboard 51 and the foot switch 52.

According to the second embodiment described above, the correction amount $\Delta T$ is set for each input method, and the B mode image data traced in response to the identified switch ID is selected as the freeze image, and thus, it is possible to select a desired image even in the case of using the plurality of freeze instruction units.

According to the second embodiment, the B mode image data is acquired by tracing back by the time obtained by adding the recognition time $T_{20}$ to the correction amount $\Delta T$ set in advance when the NUI 53 inputs the freeze instruction. Thus, it is possible to select the desired image even in the case of using the input unit that requires time until recognizing the freeze instruction as compared to the keyboard 51 and the foot switch 52.

In the above-described second embodiment, the NUI 53 is the microphone (voice input) that detects the voice. However, the NUI 53 may be a non-contact user interface that detects a gesture (motion of the practitioner) or gaze and outputs a recognition result thereof. When the NUI 53 recognizes the gesture, the NUI recognition unit 39 outputs an instruction command according to the gesture as the recognition result. In addition, when the NUI 53 recognizes the gaze (for example, captures an eye (gaze)), the NUI recognition unit 39 outputs an instruction command according to the gaze (movement of gaze) as the recognition result.

Third Embodiment

Figure 9:
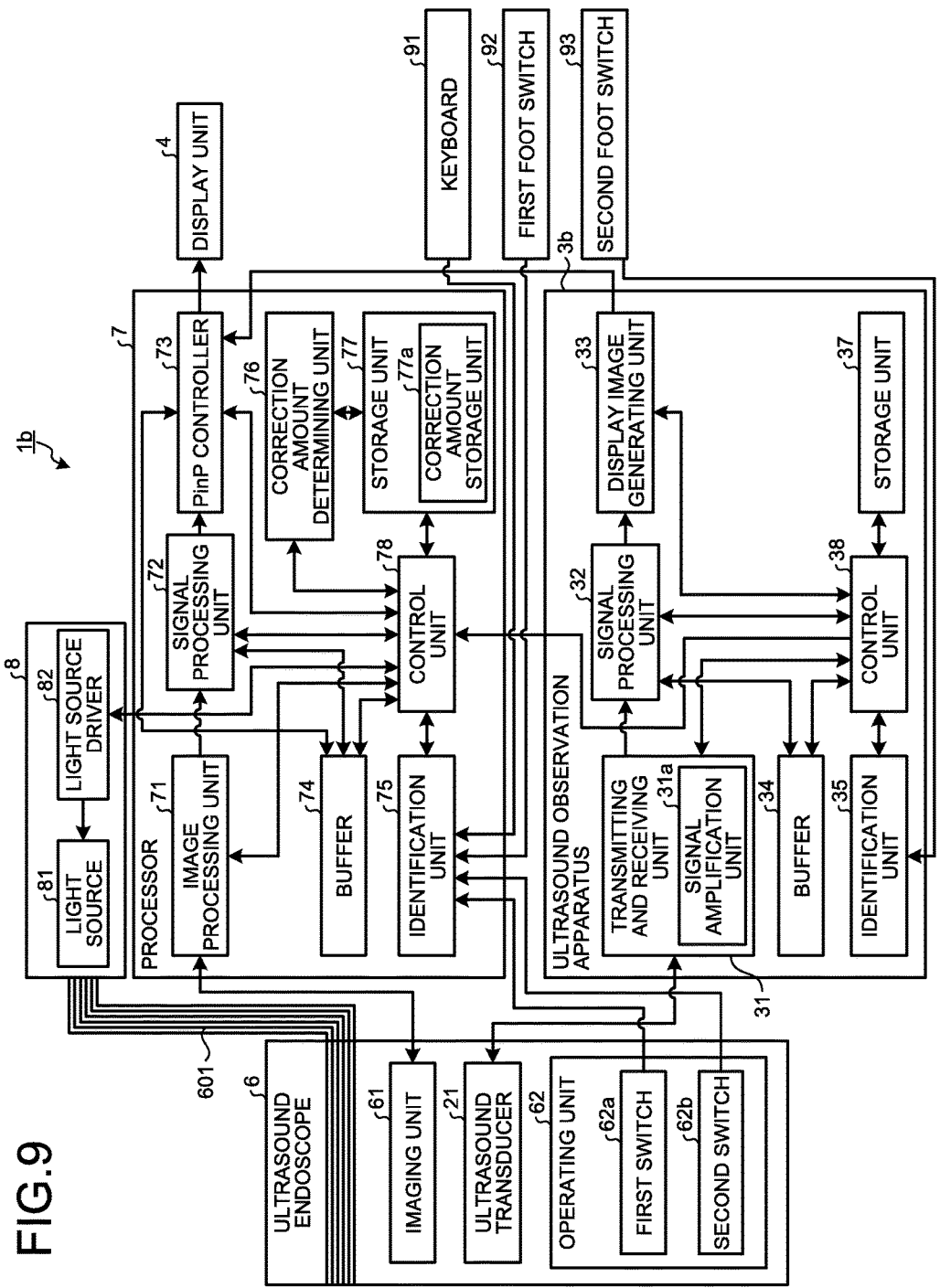
FIG. 9 is a block diagram illustrating a configuration of an ultrasound endoscopic system according to a third embodiment of the present invention.

Next, a third embodiment of the present invention will be described. FIG. 9 is a block diagram illustrating a configuration of an ultrasound endoscopic system according to the third embodiment. The same reference signs are used to designate the same elements as those of the above-described embodiments. In the above-described first embodiment, the exemplary ultrasound diagnostic system that is the device for observing the observation target using the ultrasound wave has been described. In the third embodiment, reference will be made to an exemplary ultrasound endoscopic system that is an ultrasound observation system including an ultrasound endoscope provided with both the above-described ultrasound transducer to transmit and receive an ultrasound signal and an image sensor to image an optical region.

An ultrasound endoscopic system 1b includes: an ultrasound endoscope 6 which outputs an ultrasound pulse and receives a reflected ultrasound echo, and images an imaging region including an output region of the ultrasound pulse to be acquired as an imaging signal; an ultrasound observation apparatus 3b which generates an image based on the ultrasound echo acquired by the ultrasound endoscope 6; a processor 7 which generates images based on, respectively, the ultrasound echo and the imaging signal acquired by the ultrasound endoscope 6; a light source device 8 which generates illumination light that is emitted from a distal end of the ultrasound endoscope 6; the display unit 4 which displays various types of information including the image based on the ultrasound echo generated by the processor 7 and the image according to the imaging signal; and a keyboard 91, a first foot switch 92, and a second foot switch 93 which are configured to performs input of various instructions including a freeze command signal.

The ultrasound observation apparatus 3b includes the transmitting and receiving unit 31, the signal processing unit 32 (image selection unit), the display image generating unit 33, the buffer 34 (first storage unit), the identification unit 35, the storage unit 37, and the control unit 38 described above.

The ultrasound endoscope 6 is configured of an insertion portion that includes an imaging unit 61, which captures an in-vivo image of a subject by being inserted into a body cavity of the subject, and the ultrasound transducer 21, which outputs the ultrasound pulse to an observation target and receives the ultrasound echo reflected from the observation target, at a distal end, and an operating unit 62 to operate the imaging unit 61 and the ultrasound transducer 21.

The imaging unit 61 is implemented using the image sensor in which pixels that generate imaging signals by receiving light and performing photoelectric conversion are two-dimensionally arrayed. Examples of the image sensor include a charge coupled device (CCD) image sensor, a complementary metal oxide semiconductor (CMOS) image sensor, and the like.

The operating unit 62 includes a bending knob to bend the distal end of the insertion portion, a treatment instrument insertion portion through which a treatment instrument such as biopsy forceps, an electric scalpel, and an inspection probe is inserted into a body cavity of a subject, and a plurality of switches serving as an operational input unit to input an operational command signal with respect to the ultrasound observation apparatus 3b. The plurality of switches include a first switch 62a configured to input a freeze instruction of the image based on the imaging signal displayed on the display unit 4, and a second switch 62b configured to input a freeze instruction of the image based on the ultrasound echo displayed on the display unit 4.

The processor 7 includes an image processing unit 71, a signal processing unit 72 (image selection unit), a picture in picture (PinP) controller 73, a buffer 74 (first storage unit), an identification unit 75, a correction amount determining unit 76 (selection designated time deciding unit), a storage unit 77, and a control unit 78.

The image processing unit 71 performs transmission and reception of an electric signal with the imaging unit 61. The image processing unit 71 is electrically connected to the imaging unit 61 to transmit an imaging condition such as an imaging timing to the imaging unit 61 and to receive the imaging signal generated by the imaging unit 61.

The signal processing unit 72 generates in-vivo image data to be displayed on the display unit 4 based on the imaging signal received by the image processing unit 71. The signal processing unit 72 executes predetermined image processing with respect to the imaging signal to generate the in-vivo image data including the in-vivo image. The in-vivo image (observation image) is a color image having each value of R (red), G (green), and B (blue), which are variables in an RGB color system employed as a color space.

The signal processing unit 72 sequentially performs signal processing with respect to the imaging signal output from the image processing unit 71, and outputs the generated in-vivo image data to the buffer 74. In addition, when there is the input of the freeze command signal of the in-vivo image, the signal processing unit 72 extracts, from the buffer 74, the in-vivo image data traced back by a correction amount based on the correction amount (correction time) determined by the correction amount determining unit 76, and outputs the extracted in-vivo image to the PinP controller 73 as a freeze image.

The PinP controller 73 acquires the in-vivo image data stored in the buffer 74, performs predetermined processing, such as decimation of data in response to a data step width set according to a display range of an image in the display unit 4 and gradation processing, to the acquired in-vivo image data, and then, outputs the processed in-vivo image data as in-vivo image data for display (image data in a normal observation mode). In addition, the PinP controller 73 performs control such that this in-vivo image data for display and B mode image data (image data in an ultrasound observation mode) transmitted from the ultrasound observation apparatus 3b are displayed on the display unit 4 at the same time. For example, the PinP controller 73 generates display image data to display a B mode image having a smaller size than an in-vivo image on the in-vivo image or around the in-vivo image and performs display control of the generated display image data or performs display control to display the freeze image between the in-vivo image and the B mode image, selected by the freeze instruction, on the display unit 4 while displaying the in-vivo image or the B mode image on the display unit 4 in real time.

The buffer 74 is implemented using, for example, a ring buffer, and stores a certain amount (a predetermined number of frames) of the in-vivo image data generated by the signal processing unit 72 in chronological order. When the capacity is insufficient (the predetermined number of frames of the in-vivo image data are stored), the predetermined number of frames of the latest in-vivo image data are stored in a time-series order by overwriting the latest in-vivo image data on the oldest in-vivo image data.

The identification unit 75 detects a signal input from the keyboard 91, the first foot switch 92, the first switch 62a, and the second switch 62b. When the detected signal is the freeze command signal of the image, the identification unit 75 identifies a freeze target image and a switch ID and outputs information relating to the switch ID to the control unit 78 together with the freeze command signal.

When there is the input of the freeze command signal of the image, the correction amount determining unit 76 determines the correction amount for selection of the in-vivo image data or the B mode image data serving as the freeze target image with reference to the storage unit 77. To be specific, the correction amount determining unit 76 determines a correction time for selection of the image data (the in-vivo image data or the B mode image data) obtained by tracing back from the B mode image at an input timing of the freeze command signal, by a predetermined time (predetermined frame), with reference to the storage unit 77 based on the freeze target image and the switch ID identified by the identification unit 75.

The storage unit 77 stores data including various programs to operate the ultrasound endoscopic system 1b, various parameters necessary for an operation of the ultrasound endoscopic system 1b, and the like. The storage unit 77 includes a correction amount storage unit 77a (second storage unit).

The correction amount storage unit 77a stores the correction time for selection of the freeze target image in association with the switch ID identified by the identification unit 75. FIG. 10 is a diagram for describing the correction amount stored in the correction amount storage unit of the ultrasound endoscopic system according to the third embodiment, and is a diagram for describing a relationship between the switch ID and the correction amount ΔT which relate to selection of the in-vivo image data (image data obtained by the imaging unit 61). FIG. 11 is a diagram for describing the correction amount stored in the correction amount storage unit of the ultrasound endoscopic system according to the third embodiment, and is a diagram for describing a relationship between the switch ID and the correction amount ΔT which relate to selection of the B mode image data (image data obtained by the ultrasound transducer 21). As illustrated in FIGS. 10 and 11, the correction amount ΔT is stored for each switch ID, and each switch ID is assigned to each of the normal observation mode and the ultrasound observation mode. The correction amount ΔT is calculated as a sum of a model delay time (model delay times $T_{11}$ to $T_{16}$) set according to each model and a correction time (correction times $T_{21}$ to $T_{26}$) that can be individually set by a practitioner or the like. Each correction amount ΔT (setting time: the model delay time+ the correction time) of the normal observation mode and the ultrasound observation mode according to the same switch ID is individually set depending on each processing time, and may be different or the same between both the modes.

In the third embodiment, the switch ID:1 is associated with the first switch 62*a* of the operating unit 62, the switch ID:2 is associated with the first foot switch 92, and the switch ID:3 is associated with a freeze instruction input key of the in-vivo image of the keyboard 91 in the normal observation mode. In the ultrasound observation mode, the switch ID:1 is associated with the second switch 62*b* of the operating unit 62, the switch ID:2 is associated with the second foot switch 93, and the switch ID:3 is associated with a freeze instruction input key of the B mode image of the keyboard 91.

The storage unit 77 stores the various programs including an operation program configured to execute an operation method of the ultrasound endoscopic system 1*b*. The operation program can be recorded in a computer-readable recording medium, such as a hard disk, a flash memory, a CD-ROM, a DVD-ROM, and a flexible disk, to be widely distributed. The above-described various programs can be acquired by download via a communication network. The communication network used here is implemented, for example, using an existing public switched telephone network, local area network (LAN), wide area network (WAN), or the like, which may be wired or wireless.

The storage unit 77 having the above-described configuration is implemented using a read only memory (ROM) in which the various programs and the like are installed in advance, a random access memory (RAM) which stores a calculation parameter and data of each processing, and the like.

The control unit 78 is implemented using a CPU, various calculation circuits, and the like having a control function. The control unit 78 reads information stored and saved in the storage unit 77 from the storage unit 77, and executes various types of calculation processing relating to the operation method of the ultrasound endoscopic system 1*b* including the ultrasound observation apparatus 3*b* so as to collectively control the ultrasound endoscopic system 1*b*.

The light source device 8 includes a light source 81 and a light source driver 82.

The light source 81 is configured using a light source that emits illumination light and one or a plurality of lenses. The light source emits light (illumination light) when being driven under control of the light source driver 82. The illumination light generated by the light source 81 is emitted from a distal end of the ultrasound endoscope 6 toward a subject via a light guide 601.

The light source driver 82 supplies a current to the light source 81 under control of the control unit 78 so as to cause the light source 81 to emit the illumination light. The control unit 78 controls the drive of the light source driver 82 to control the amount of power to be supplied to the light source 81 and control a drive timing of the light source 81.

The keyboard 91 is provided with a plurality of keys, and outputs a signal in response to the key when the key is pressed. The keyboard 91 may be configured to implement the plurality of keys using a touch panel, and to include a display unit to display the image.

Each of the first foot switch 92 and the second foot switch 93 includes a bar that receives input of a signal when being stepped on by a foot. In the third embodiment, when the practitioner steps on the bar, the freeze command signal of the image is received. The freeze command signal is input to the identification unit 75 in a case where the first foot switch 92 is stepped on, and the freeze command signal is input to the identification unit 35 in a case where the second foot switch 93 is stepped on.

In the third embodiment, the identification unit 35 receives input of the signal from the second foot switch 93 and outputs the received signal to the control unit 38 as the freeze command signal. The control unit 38 outputs the freeze command signal output from the identification unit 35 to the control unit 78.

Figure 12:
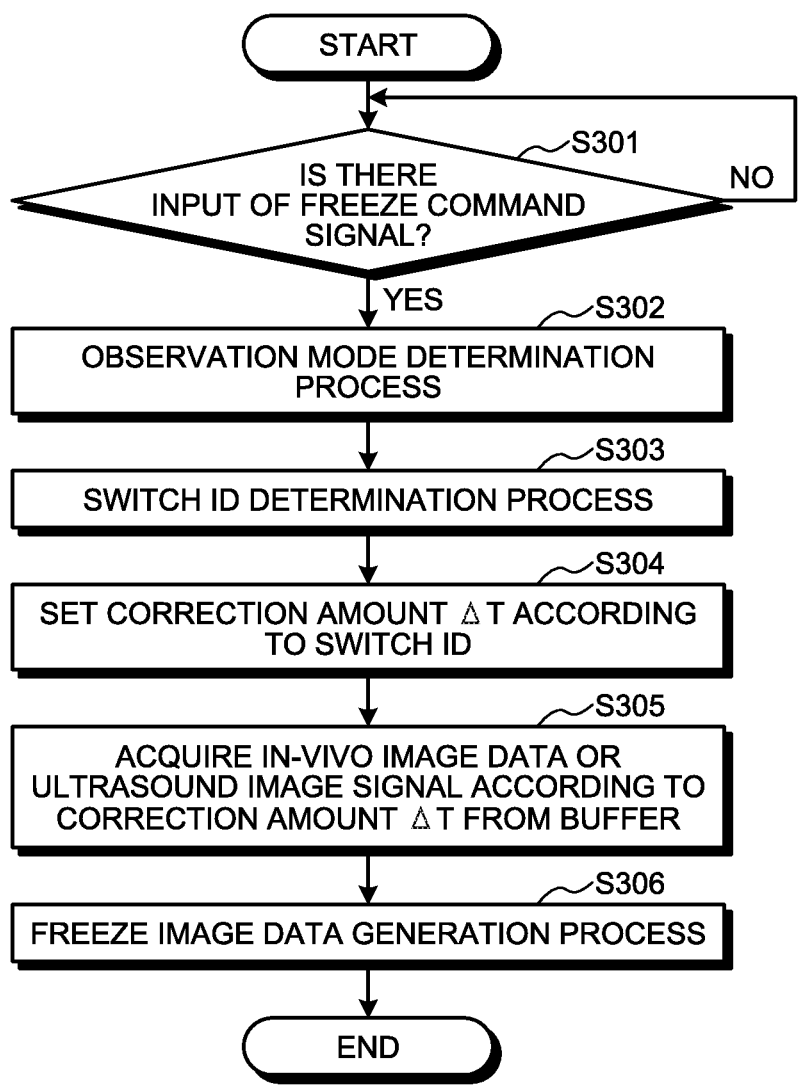
FIG. 12 is a flowchart for describing a freeze image generation process performed by the ultrasound endoscopic system according to the third embodiment of the present invention.

Next, reference will be made to a freeze image generation process that is performed by the ultrasound endoscopic system 1*b* having the above-described configuration with reference to the drawings. FIG. 12 is a flowchart for describing the freeze image generation process performed by the ultrasound endoscopic system according to the third embodiment.

First, the control unit 78 determines whether there is the input of the freeze command signal (Step S301). When there is the input of the freeze command signal (Step S301: Yes), the control unit 78 proceeds to Step S302. On the contrary, when there is no input of the freeze command signal (Step S301: No), the control unit 78 returns to Step S301 and repeatedly checks the input of the freeze command signal.

When transitioning to Step S302, the control unit 78 performs a determination process on whether an image as a freeze instruction target is the in-vivo image (the normal observation mode) or the B mode image (the ultrasound the observation mode). To be specific, for example, the identification unit 75 determines whether the observation mode is the normal observation mode or the ultrasound observation mode, or determines whether the device (or the key) that has input the signal instructs freeze of the in-vivo image (the normal observation mode) or freeze of the B mode image (the ultrasound the observation mode) based on information assigned to the freeze command signal.

After determining the image as the freeze instruction target, the control unit 78 determines the switch ID of the switch that has input the freeze command signal (Step S303). The control unit 78 causes the identification unit 75 to identify the switch ID assigned to the freeze command signal. When obtaining an identification result from the identification unit 75, the control unit 78 outputs the identification result (the switch ID) and the information (observation mode and the like) relating to the freeze target image to the correction amount determining unit 76, and proceeds to Step S304.

In Step S304, the correction amount determining unit 76 determines the correction amount, and performs setting of the determined correction amount (the correction amount ΔT). To be specific, the correction amount determining unit 76 refers to the correction amount storage unit 77a based on the switch ID identified by the identification unit 75 to output the correction amount ΔT, and sets the correction amount ΔT corresponding to the freeze command signal.

When the correction amount determining unit 76 sets the correction amount ΔT, the control unit 78 outputs the correction time ΔT to the signal processing unit 72 to cause the in-vivo image data to be output from the buffer 74 in a case where the image as the freeze instruction target is the in-vivo image (the normal observation mode), and outputs the correction amount ΔT to the control unit 38 (the signal processing unit 32) to cause the B mode image data (the ultrasound image signal) to be output from the buffer 34 in a case where the image as the freeze instruction target is the B mode image (the ultrasound the observation mode) (Step S305).

Thereafter, the PinP controller 73 performs predetermined signal processing on the freeze image data (the in-vivo image data or the B mode image data) output from the signal processing unit 72 or the signal processing unit 32, and performs a process of generating freeze image data for display (Step S306). The PinP controller 73 performs control such that the generated freeze image is displayed in the state of being superimposed inside an image being displayed in real time, thereby displaying the selected freeze image on the display unit 4.

The in-vivo image or the B mode image as the freeze image, generated by performing the freeze image generation process as described above, enables acquisition of the in-vivo image data or the B mode image data traced back by each correction amount (setting time) with respect to the freeze instruction input by any of the plurality of switches (switches ID:1 to 3), and thus, it is possible to display the freeze image that the practitioner desires on the display unit 4.

According to the third embodiment described above, the correction amount ΔT is set for each of the plurality of switches, and the image data traced in response to the identified switch ID is selected as the freeze image, and thus, it is possible to select a desired image even in the case of using the plurality of freeze instruction units.

According to the third embodiment, each correction amount is set according to the normal observation mode to observe the in-vivo image or the ultrasound observation mode to observe the B mode image and the freeze target image is selected by the identification unit 75 in response to the identification result, and thus, it is possible to select the desired image regardless of the observation mode.

The NUI 53 and the NUI recognition unit 39 according to the above-described second embodiment may be further provided in the third embodiment. In this case, it is preferable to provide the NUI recognition unit 39 in the processor 7.

In the third embodiment, the observation mode and the switch ID are identified by the identification unit 75 provided on the processor 7 side, and the correction amount determining unit 76 performs the setting of the correction amount. However, the identification unit and the correction amount determining unit may be provided on the ultrasound observation apparatus 3b side, or the identification unit and the correction amount determining unit may be provided to each of the processor 7 and the ultrasound observation apparatus 3b. In addition, a signal output destination of the device (or the key), which performs the input of the freeze instruction, may be set, in advance, in the ultrasound observation apparatus 3b or the processor 7 according to the image as the freeze instruction target (the in-vivo image or the B mode image).

The display unit 4 and the keyboard 91 are connected to the processor 7 side in the third embodiment, but may be connected to the ultrasound observation apparatus 3b or may be connected to both the processor 7 and the ultrasound observation apparatus 3b.

The PinP controller 73 is provided in the processor 7 in the third embodiment, but may be provided in the ultrasound observation apparatus 3b.

In the third embodiment, the exemplary ultrasound observation system using the endoscope has been described. However, an ultrasound observation system that includes a fixed-point camera for capturing an observation region and the above-described ultrasound diagnostic system 1 or 1a may be employed, for example.

In the above-described first to third embodiments, the keyboard 51 or 91, the foot switch 52, the NUI 53, and the like are used as the input units of the freeze instruction. However, a mouse, a touch panel, a lever, or the like may be used as the input units, and combinations thereof may be used.

In the above-described first to third embodiments, both an ultrasound image and an endoscopic image are displayed on the display unit 4. However, the images may be separately displayed on two different display units.

In the above-described first to third embodiments, the correction amount storage unit 37a or 77a stores the correction amount in association with the switch ID. However, when a plurality of users (for example, practitioners) use the system, it is preferable to store the correction amount for each of the plurality of users. When the correction amount for each user is stored and the user using the ultrasound diagnostic system 1 or 1a or the ultrasound endoscopic system 1b calls the own correction amount from the correction amount storage unit 37a or 77a, it is possible to perform selection of the freeze image according to the correction amount individually set for each user.

In the above-described first to third embodiments, the observation target is the body tissue. However, an industrial endoscope for observing characteristics of material may be employed. The medical diagnostic apparatus according to the present invention can be applied to both the inside and outside of a body. The observation target may be irradiated with infrared light instead of the ultrasound wave to transmit and receive the signal of the observation target.

According to some embodiments, it is possible to select the desired image even in the case of using the plurality of freeze instruction units.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical diagnostic apparatus for acquiring a signal to generate images of an observation target, sequentially generating a plurality of observation images based on the acquired signal, and causing an external display unit to continuously display the plurality of observation images, the medical diagnostic apparatus comprising:

a first storage unit configured to store the plurality of observation images in chronological order;

a plurality of freeze instruction input units configured to receive a command signal for freezing the plurality of observation images on the display unit;

a second storage unit configured to store correction information for each of the plurality of freeze instruction input units so as to associate the correction information with each of the plurality of freeze instruction input units in advance;

an identification unit configured to identify a freeze instruction input unit that has received the command signal among the plurality of freeze instruction input units;

a correction amount determining unit configured to determine a correction amount based on a result of identification by the identification unit and the correction information stored in the second storage unit; and an image selection unit configured to select an observation image generated before receiving the command signal according to the correction amount or an observation image generated after receiving the command signal according to the correction amount, from among the plurality of observation images stored in the first storage unit, based on the correction amount determined by the correction amount determining unit.

2. The medical diagnostic apparatus according to claim 1, wherein
the correction amount is time or the number of frames.

3. The medical diagnostic apparatus according to claim 1, wherein
the second storage unit is configured to further store a model delay time according to a signal processing time for each of the plurality of freeze instruction input units,
the correction information indicates time to adjust an increase or a decrease in the model delay time, and
the image selection unit is configured to select the observation image based on the correction amount including at least a sum of the model delay time and the correction information.

4. The medical diagnostic apparatus according to claim 3, wherein
the correction amount is a sum of a setting time and a uniform adjustment time, the setting time being defined by the sum of the model delay time and the correction information, the uniform adjustment time being defined as uniformly adjusting an increase or a decrease in the correction amount relating to the plurality of freeze instruction input units.

5. The medical diagnostic apparatus according to claim 1, wherein
the plurality of freeze instruction input units includes a non-contact user interface.

6. The medical diagnostic apparatus according to claim 5, wherein
when the identification unit identifies the freeze instruction input unit that has received the command signal as the non-contact user interface, the correction amount determining unit is configured to set, as the correction amount, a sum of a setting time associated with the non-contact user interface stored in the second storage unit and a recognition time between a processing start time of the non-contact user interface and completion of receiving the command signal.

7. The medical diagnostic apparatus according to claim 4, wherein
the correction amount differs depending on image quality or a frame rate of the observation image.

8. The medical diagnostic apparatus according to claim 1, wherein
the signal to generate the images of the observation target is generated based on an echo signal obtained by converting an ultrasound echo into an electric signal, the ultrasound echo being obtained by transmitting an ultrasound wave to the observation target and receiving the ultrasound wave reflected from the observation target.

9. The medical diagnostic apparatus according to claim 8, wherein
the signal to generate the images of the observation target further includes an imaging signal obtained by converting an optical signal received by an image sensor into an electric signal, and
the correction information for each of the plurality of freeze instruction input units is different between the echo signal and the imaging signal.

10. A method for operating a medical diagnostic apparatus for acquiring a signal to generate images of an observation target, sequentially generating a plurality of observation images based on the acquired signal, and causing an external display unit to continuously display the plurality of observation images, the method comprising:

receiving, by a first freeze instruction input unit or a second freeze instruction input unit different from the first freeze instruction input unit, a command signal for freezing the plurality of observation images on the display unit;

identifying, by an identification unit, which of the first and second freeze instruction input units have received the command signal;

determining, by a correction amount determining unit, a correction amount based on a result of identification; and selecting, by an image selection unit, an observation image generated before receiving the command signal according to the correction amount or an observation image generated after receiving the command signal according to the correction amount, from among the plurality of observation images in accordance with the result of identification.

11. A non-transitory computer-readable recording medium with an executable program stored thereon for operating a medical diagnostic apparatus for acquiring a signal to generate images of an observation target, sequentially generating a plurality of observation images based on the acquired signal, and causing an external display unit to continuously display the plurality of observation images,
the program causing the medical diagnostic apparatus to execute:

receiving, by a first freeze instruction input unit or a second freeze instruction input unit different from the first freeze instruction input unit, a command signal for freezing the plurality of observation images on the display unit;

identifying, by an identification unit, which of the first and second freeze instruction input units have received the command signal;

determining, by a correction amount determining unit, a correction amount based on a result of identification; and selecting, by an image selection unit, an observation image generated before receiving the command signal according to the correction amount or an observation image generated after receiving the command signal according to the correction amount, from among the plurality of observation images in accordance with the result of identification.

* * * * *